United States Patent [19]
Turriff et al.

[11] Patent Number: 5,522,271
[45] Date of Patent: Jun. 4, 1996

[54] TOOL AND METHOD FOR SOIL SAMPLING

[75] Inventors: David E. Turriff; Lloyd E. Jacobs; Nils K. Melberg; Christopher A. Reitmeyer, all of Green Bay, Wis.

[73] Assignee: En Chem, Inc., Green Bay, Wis.

[21] Appl. No.: 505,825

[22] Filed: Jul. 21, 1995

[51] Int. Cl.$^6$ ............................................. G01N 1/04
[52] U.S. Cl. ..................... 73/864.44; 73/864.45
[58] Field of Search ......................... 73/864.44, 864.45, 73/864.91; 175/58, 403, 20, 249, 257; 408/68; 220/265, 266, 277, 278

[56] References Cited

U.S. PATENT DOCUMENTS

| | | | |
|---|---|---|---|
| 1,737,718 | 12/1929 | Hausman | 220/266 |
| 2,288,210 | 6/1942 | Schlumberger | 175/403 |
| 3,326,049 | 6/1967 | Eley | 73/864.44 |
| 3,412,814 | 11/1968 | Rosfelder | 73/864.45 |
| 3,497,018 | 2/1970 | Shultz et al. | 175/20 |
| 4,549,612 | 10/1985 | Cushing | 175/20 |
| 4,729,437 | 3/1988 | Zapico | 175/20 |
| 4,819,735 | 4/1989 | Puckett | 172/22 |
| 4,989,678 | 2/1991 | Thompson | 73/864.44 |
| 5,343,771 | 9/1994 | Turriff et al. | 73/864.44 |

*Primary Examiner*—Robert Raevis
*Attorney, Agent, or Firm*—Jansson & Shupe, Ltd.

[57] ABSTRACT

Disclosed is a soil sampling tool having a barrel and a plug in the barrel for expelling a soil sample from the barrel. In the improvement, the plug is imperforate and includes a frangible section attached to the barrel. When the soil sample is expelled as, e.g., into a lab vial, force is applied to the plug, breaking the frangible section and urging the plug and the soil sample out of the barrel. Since it is imperforate, the plug prevents VOC vapors from migrating out of the mouth portion and the barrel is thereby made suitable for a single use and is disposable. The advantages include avoidance of sample "cross-contamination." A new method for analyzing a soil sample including the steps of providing a sampling tool having a barrel, a mouth portion and a plug retained in the barrel by a frangible section. The mouth portion is filled with a soil sample and the plug is urged toward the mouth portion, thereby breaking the frangible section and expelling the soil sample from the tool.

21 Claims, 6 Drawing Sheets

TOOL AND METHOD FOR SOIL SAMPLING

FIELD OF THE INVENTION

This invention relates generally to measuring and testing and, more particularly, to sampling of soil for the presence of a volatile organic compound (VOC).

BACKGROUND OF THE INVENTION

Soil sampling tools and devices are used for a variety of purposes, e.g., to obtain samples for soil moisture content or to detect and analyze a VOC which may have permeated the soil. And soil cores are removed for other reasons unrelated to VOC analysis. Examples of soil coring and sampling tools are shown in U.S. Pat. Nos. 3,326,049 (Eley); 3,444,938 (Ballman); 3,497,018 (Schultz et al.) and 4,989,678 (Thompson) and others.

It is common knowledge that tanks for storing liquids may, over time, develop a leak. If the tank is above ground, the leak is usually observed rather soon after its onset and not much damage results. On the other hand, there is an already-substantial and growing awareness that certain types of liquid storage tanks placed underground have a greater-than-normal propensity to deteriorate and leak. Such types include tanks made of common sheet steel which had no protective coating or from which such coating has been eaten away. And a substantial factor contributing to the risk of tank leakage is that with an underground tank, leakage is not visible. Usually, such leakage can only be detected by excavation and testing.

And the risks are enormous. Undetected leaks of underground storage tanks can and do contaminate soil and potable water supplies, the latter by polluting underground aquifers from which a great deal of drinking water is drawn. Recent legislation recognizes risks presented by leaking underground storage tanks and provides for remediation of damage caused by such leaks. Because of the number of gasoline service stations and private fuel and solvent storage tanks, leakage of petroleum distillates and hydrocarbons is a particularly significant problem.

Good remediation requires that personnel be able to accurately determine the nature of the fluid involved in the leak and the extent (depth and area) to which such fluid has permeated the earth and, perhaps, polluted water. Such determination depends in large part upon the availability of high quality test instruments and the ability to preserve the integrity of a soil sample. Preservation of integrity involves (among other factors) prevention of evaporation of VOCs in a soil sample. The efforts of earlier workers in this regard have not been entirely satisfactory.

For example, known sampling tools are made of metal, preferably stainless steel. In instances where dozens or even hundreds of soil samples are taken at a particular site, the sheer aggregate weight of the tools imposes a burden upon their users.

Another disadvantage of known metal sampling tools is that they are made by machining metal stock. The cost of such tools, especially if made available in quantities of hundreds of tools per site, is quite considerable.

Still another disadvantage of known soil sampling tools is that after use, they must be thoroughly washed to help avoid so-called "cross-contamination," i.e., contamination of the next-successive sample collected by residue left on the tool from the preceding sample collected. And even though washing is a major factor in preventing such cross-contamination, the time required to perform thorough washing of, e.g., several hundred tools, can be substantial.

Yet another disadvantage of known tools involves the fact that over time and repeated use, critical VOC-sealing surfaces may become scratched or otherwise impaired. Surface impairments such as scratches can form small passages from which VOC vapors can escape, impairing the integrity of the sample.

An improved tool which addresses and overcomes disadvantages of prior art tools would be an important advance in the art.

OBJECTS OF THE INVENTION

It is an object of the invention to provide an improved soil sampling tool overcoming some of the problems and shortcomings of the prior art.

Another object of the invention is to provide a soil sampling tool which preserves the integrity of the VOC in a soil sample.

Yet another object of the invention is to provide a soil sampling tool which helps avoid sample cross-contamination.

Another object of the invention is to provide a soil sampling tool

Another object of the invention is to provide a soil sampling tool which is light in weight.

Still another object of the invention is to provide a soil sampling tool which is lower in cost.

Another object of the invention is to provide a soil sampling tool which is substantially free of surface impairments and provided consistent sampling results.

Another object of the invention is to provide a soil sampling tool which is made of a moldable material such as plastic.

Another object of the invention is to provide a soil sampling tool which is suitable for a single use and is disposable (preferably by recycling) after such use.

Yet another object of the invention is to provide a new method for collecting a soil sample. How these and other objects are accomplished will become apparent from the following descriptions and the drawings.

SUMMARY OF THE INVENTION

The invention involves a soil sampling tool of the type having a barrel and a plug in the barrel for expelling a soil sample therefrom. In the improvement, the plug includes a frangible section attached to the barrel. The frangible section is broken during expulsion of a soil sample from the barrel and the barrel is thereby suitable for a single use and disposable after such use.

The barrel includes a mouth portion and a generally tubular column member, the latter used to apply force to the mouth portion and urge such portion into soil. The plug is between the mouth portion and the column member and provides an imperforate seal therebetween. Vapors of VOCs in the mouth portion are thereby prevented from migrating to the column member and impairing the integrity of the soil sample. In a specific yet highly preferred embodiment, the mouth portion has a fixed volumetric capacity, e.g., 25–30 grams, depending upon the parameters of the regulatory program with which the tool is being used.

The new tool also has a cap for closing the mouth portion after collection of a sample. There is a cap retention mechanism securing the cap with respect to the barrel. In one specific embodiment, the barrel has a longitudinal axis and the cap retention mechanism includes at least one retention arm extending generally parallel to the axis and securing the cap with respect to the barrel.

In a highly preferred embodiment, there is a pair of retention arms attached to the cap. The barrel has a pair of surface distortions for engagement by respective retention arms. In a specific embodiment, at least one retention arm has a hook-like end and at least one of the surface distortions includes a tang extending from the barrel for engagement by such hook-like end. For optimum sample integrity, the cap has a seal engaging the mouth portion, whereby the vapors are substantially prevented from escaping from the mouth portion.

In another aspect of the invention, the tool has a support member contacting the plug, whereby the frangible section is prevented from breaking during collection of a soil sample. That is, the support member "backs up" or "reinforces" the plug to prevent the force of the soil sample pushing against the plug from rupturing the frangible section.

In a specific exemplary embodiment, the barrel has a grasping portion, the support member has a holding component and the holding component is aligned with the grasping portion during sample collection. The grasping portion includes a handle-like lateral extension and the holding component contacts and abuts against the lateral extension during collection of a soil sample. Most preferably, the grasping portion and the holding component are T-shaped and abut during sample collection. In that way, a user is able to easily grasp such portion and such component and retain them against one another while urging the tool into soil.

The new tool also has a sample expulsion device for urging a soil sample out of the mouth portion when such sample is being prepared for laboratory analysis or for any other reason. In a highly preferred embodiment, the barrel and the expulsion device are cooperatively configured to have certain dimensional relationships.

Specifically, the mouth portion has a cutting edge and the barrel has a distal portion spaced at a first distance from the cutting edge. The expulsion device has a proximal end and a distal portion spaced at a second distance from the proximal end and the second distance is greater than the first distance. In that way, the expulsion device has sufficient length to entirely urge the plug (and the soil sample) from the barrel when expelling such sample from the mouth portion.

The new tool also includes a feature which helps prevent the plug (which, during sample expulsion, is freed from attachment to the barrel) from falling into a laboratory vial intended to receive only the soil sample. The plug and the proximal end of the expulsion device each has a surface deformity and such deformities coact to retain the plug when the plug is urged from the barrel. In one specific embodiment, each of the surface deformities includes a tongue component and a groove component. Such components are sized, shaped and located so that the tongue component of one engages the groove component of the other and vice versa.

Further, such engagement is with a slight press or "friction" fit so that once engaged, the plug is retained on the expulsion device against the force of gravity. That is, the plug does not fall into the lab vial when such plug "clears" the cutting edge of the mouth portion. Rather, such plug must be intentionally removed from the expulsion device.

A new method for collecting a soil sample including the steps of providing a sampling tool having a barrel, a mouth portion and a plug retained in the barrel by a frangible section. The mouth portion is filled with a soil sample (by urging such portion into soil) and the plug is urged toward the mouth portion, thereby breaking the frangible section.

In more specific aspects of the method, the filling step includes preventing the frangible section from breaking and the preventing step includes contacting the plug with a support member. The filling step is followed by the steps of fitting a cap to the mouth portion and engaging a cap retention arm with a surface distortion for holding the cap on the mouth portion and preventing escape of VOC vapors.

In another specific aspect of the method, the urging step includes extending the proximal end of the expulsion device into the barrel, engaging the surface deformities with one another and expelling the soil sample from the mouth portion. With the surface deformities engaged, the plug is retained at the proximal end of the expulsion device upon sample expulsion.

Other details of the invention are set forth in the following detailed description and in the drawings.

BRIEF DESCRIPTION OF THE DRAWINGS

FIG. 21 is a second embodiment of an arrangement for retaining the tool plug on the expulsion device. Parts are shown in dashed outline.

FIG. 22 is a third embodiment of an arrangement for retaining the tool plug on the expulsion device. Parts are in cross-section and other parts are broken away.

DETAILED DESCRIPTION OF PREFERRED EMBODIMENTS

Figure 1:
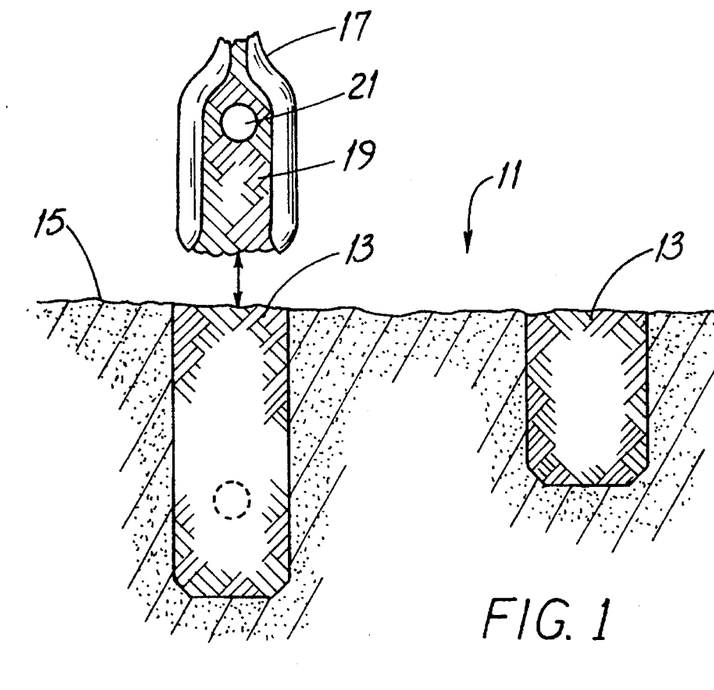
FIG. 1 is a cross-sectional elevation view of the earth showing two holes and a split spoon device used in taking soil samples.
Figure 2:
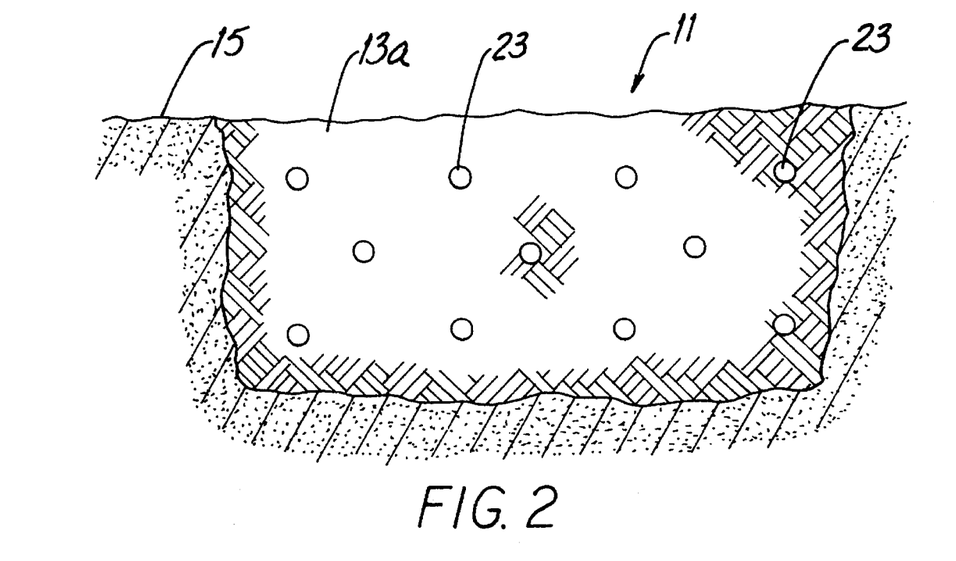
FIG. 2 is a cross-sectional elevation view of the earth showing a larger pit-like hole used in taking soil samples.

Before describing the new sampling tool 10, it will be helpful to have an understanding of how the tool 10 is used to evaluate the degree, if any, to which a site is contaminated by a VOC. Referring to FIGS. 1 and 2, it is assumed that the site 11 of a suspected leaking underground storage tank has been identified. Determination as to whether and to what extent the site 11 is contaminated by a VOC is by boring holes 13 (to avoid sampling at the earth surface 15 where a VOC and its vapors may be less concentrated) and use a split spoon device 17 (resembling a plug-type post hole digger) to extract relatively-large "slugs" 19 of soil from various holes 13. Using the tool 10, a soil sample is taken from a location 21 (or perhaps two or more locations) on the slug 19. Each slug 19 is removed from a known depth and leaves a hole having a known location 13. Both such informational items are recorded for "mapping" the site 11 with a field sketch.

Figure 3:
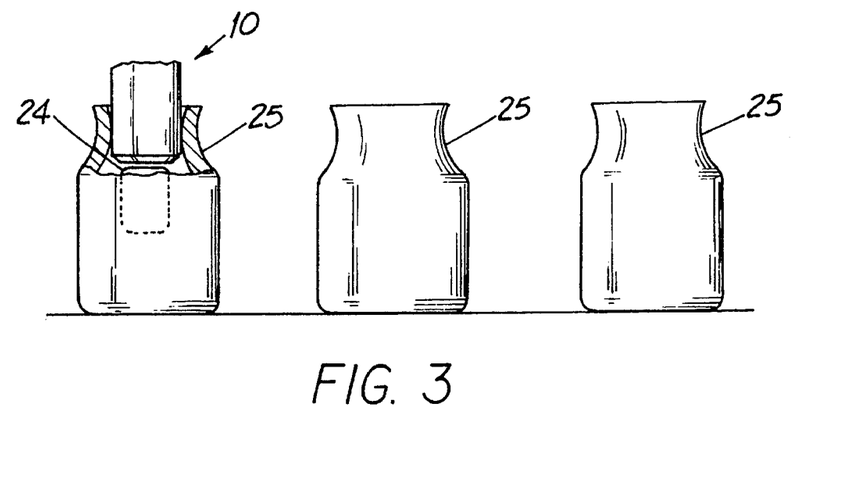
FIG. 3 is a representative side elevation view showing a soil sample being expelled into one of plural vials used for sample analysis. Parts are broken away.

In another approach, a larger hole 13a is dug in the earth and soil samples are taken at various horizontally and vertically spaced locations 23 along the generally vertical wall of the hole 13a and, probably, at other locations. The wall and the locations will similarly be mapped with a field sketch. As shown in FIG. 3, the "sample-loaded" tools 10 are used to place soil samples into vials, the contents of which are analyzed in a laboratory.

Figures 4, 5:
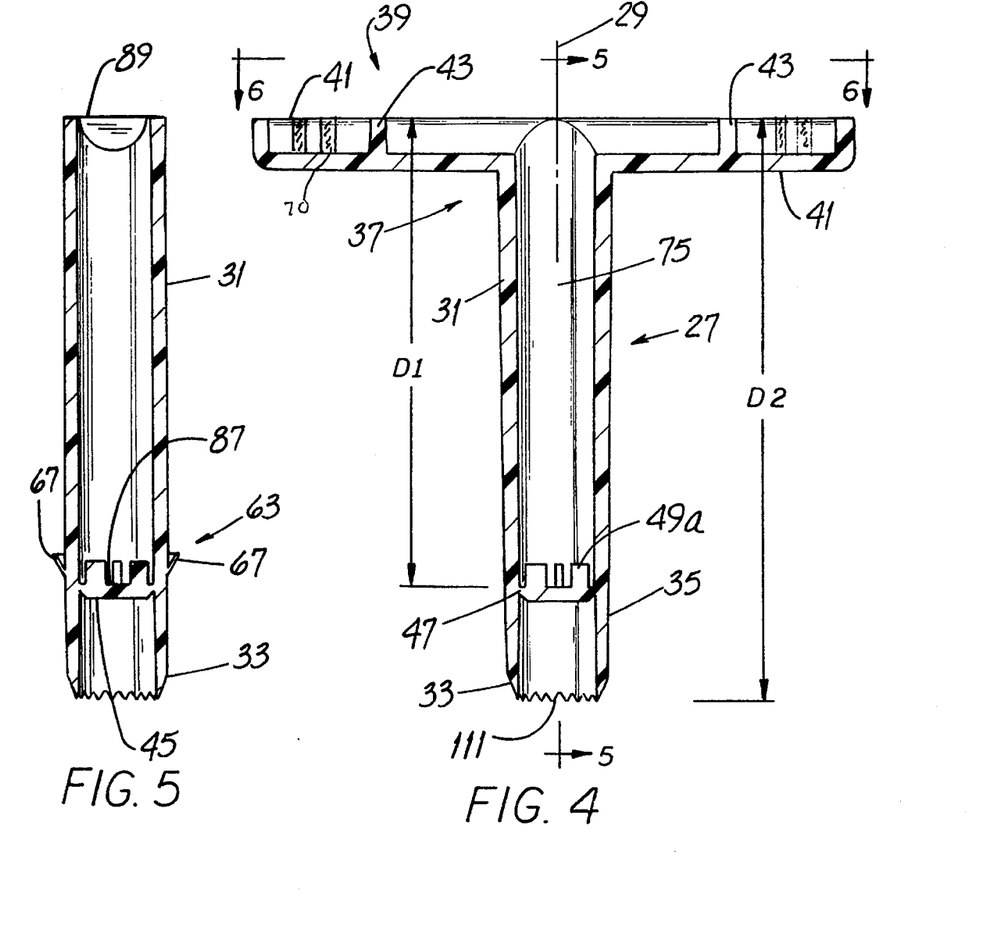
FIG. 4 is a cross-sectional elevation view of the barrel portion of the new sampling tool.
FIG. 5 is a cross-sectional view of the barrel portion of FIG. 4 taken generally along the viewing plane 5—5 thereof.
Figure 6:
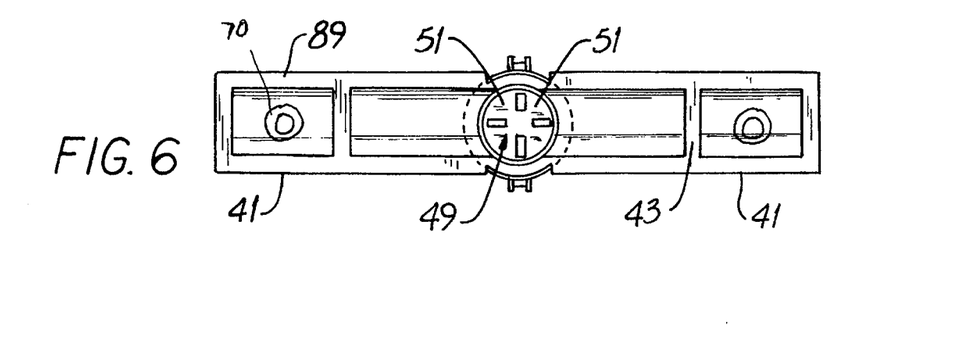
FIG. 6 is a top plan view of the barrel portion of FIG. 4 taken generally along the viewing plane 6—6 thereof.

Referring also to FIGS. 4, 5 and 6, aspects of the new sampling tool 10 and a new method for collecting a soil sample will now be described. The new tool 10 has an elongate, generally tubular barrel 27 extending along a long axis 29 and having a column member 31 and a mouth portion 33 at the barrel distal end 35. Such column member 31 is used to apply force to the mouth portion 33 and urge such portion 33 into soil.

At its proximal end 37, the barrel 27 has a grasping portion 39, preferably embodied as a pair of oppositely-directed lateral extensions 41. Such extensions 41 and the barrel 27 define a generally T-shaped structure and the handle-like extensions 41 are useful when urging the mouth portion 33 into soil. In the exemplary embodiment shown in FIG. 6, each of the extensions 41 is half-cylindrical and includes one or more reinforcing ribs 43 spaced therealong.

Referring also to FIGS. 4 and 5, the barrel 27 has a plug 45 positioned between the mouth portion 33 and the column member 31. Such plug 45 is imperforate, i.e., free of holes. Vapors of a VOC in the mouth portion 33 are thereby prevented from migrating to the column member 31. (Migration of such vapors impairs the integrity of the soil sample by reducing the apparent concentration of the VOC in the sample 24.)

The plug 45 includes an annular frangible section 47 attached to the barrel 27. Such section 47 is preferably a thin web which may be rather easily broken during expulsion of a soil sample as described below. Of course, once the section 47 is broken, the utility of the barrel 27 for soil sampling is destroyed. Thus, the barrel 27 is suitable for but a single use and is disposable after such use.

For reasons relating to plug retention during sample expulsion (as described below), the plug 45 includes one or more surface deformities 49, e.g., at least one (and preferably two or more) axially-projecting tongue components 49a separated by groove components 51. During sample expulsion, such tongue components 49a engage groove components 53 in an expulsion device 55 (FIGS. 12, 13) and retain the plug 45 to such device 55.

Referring also to FIGS. 7, 8, 14, 15 and 16, the new tool 10 also has a cap 57 for closing the mouth portion 33 after collection of a sample. After sample collection, a cap retention mechanism 59 secures the cap 57 with respect to the barrel 27. In one specific embodiment, the cap retention mechanism 59 includes at least one retention arm 61 extending generally parallel to the barrel axis 29.

In a highly preferred embodiment, there is a pair of retention arms 61 attached to the cap 57 and spaced about 180° from one another. The barrel 27 has a pair of surface distortions 63 for engagement by respective retention arms 61. In a specific embodiment, at least one retention arm 61 has a hook-like end 65 and at least one of the surface distortions 63 includes a tang 67 extending radially from the barrel 27 for engagement by such hook-like end 65. For optimum sample integrity, the cap 57 has a groove-retained resilient seal ring 69 engaging the mouth portion 33 to substantially prevent VOC vapor from escaping from such portion 33.

Figures 9, 10:
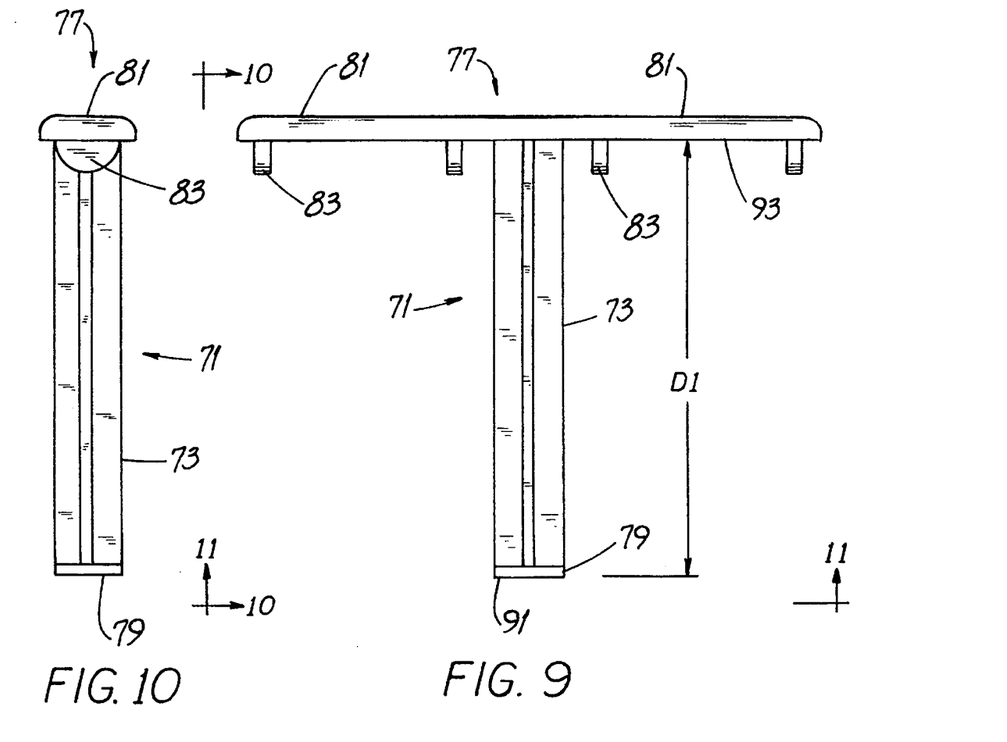
FIG. 9 is an elevation view of the tool support member.
FIG. 10 is an elevation view of the tool support member of FIG. 9 taken generally along the viewing plane 10—10 thereof.
Figure 11:
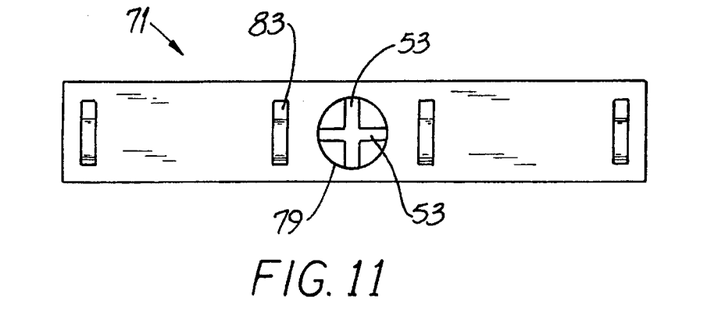
FIG. 11 is a view of the tool support member of FIG. 9 taken generally along the viewing plane 11—11 thereof.

Referring also to FIGS. 9, 10 and 11 the tool 10 has a support member 71 with a rod portion 73 sized to extend into the barrel passage 75 with slight clearance. At its proximal end 77, such portion 73 has a holding component 79, e.g., a pair of oppositely-directed lateral extensions 81 similar in length to the barrel extensions 41. Such extensions 81 and the rod portion 73 also define a generally T-shaped structure.

And like the barrel extensions 41, the extensions 81 of the support member 71 each have one or more reinforcing ribs 83 disposed therealong. Of course, the ribs 43 of the barrel 27 and those of the support member 71 are preferably cooperatively located so that they do not interfere with one another when the barrel 27 and the support member 71 are assembled to one another.

Figures 7, 8:
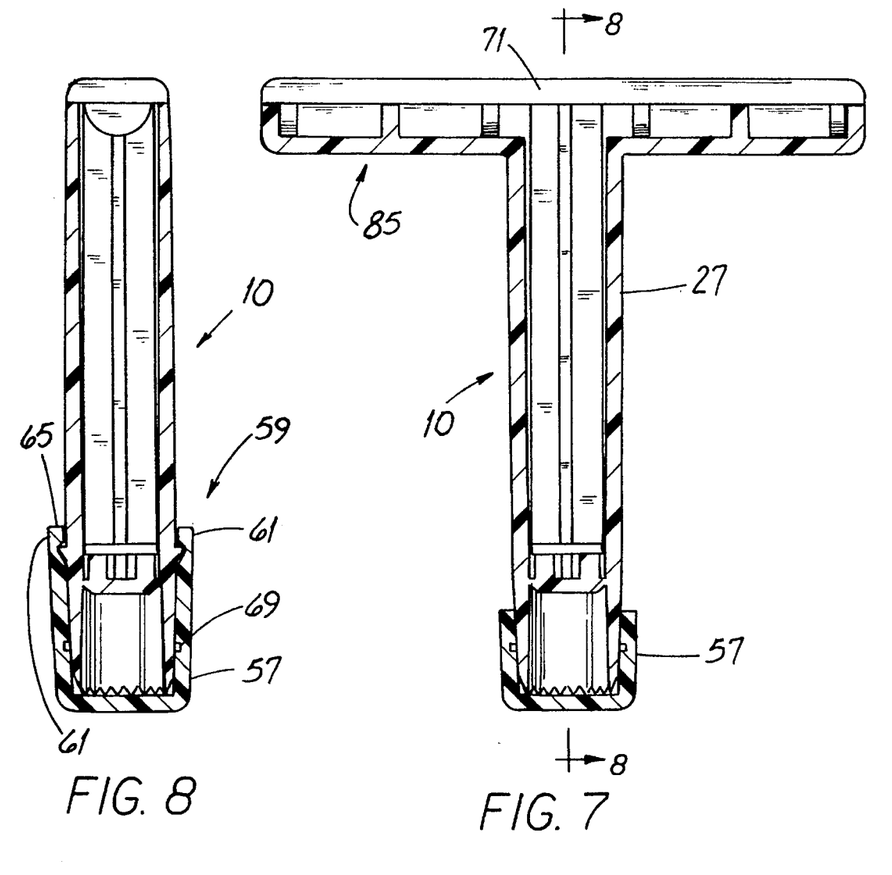
FIG. 7 is a cross-sectional elevation view of the barrel portion of FIG. 4, the support member of FIG. 9 and the cap of FIGS. 14, 15 and 16 assembled to one another. Parts are shown in full representation.
FIG. 8 is a cross-sectional view of the assembly of FIG. 7 taken generally along the viewing plane 8—8 thereof. Parts are shown in full representation.

Referring to FIGS. 4, 6, 7, 9 and 11, the support member 71 preferably includes male holding pins 68 which extend into female holding studs 70 when the member 71 and barrel 27 are assembled to one another as shown in FIG. 7. The member 71 and barrel 27 are thereby retained assembled during shipping and handling and a tool notch 72 is provided for prying the member 71 and barrel 27 apart.

When such barrel 27 and support member 71 are assembled to one another as shown in FIGS. 7 and 8, the grasping portion 39 of the barrel 27 and the holding component 79 of the support member 71 abut one another and form a convenient handle 85. In a highly preferred embodiment, the barrel 27 and support member 71 are configured with specific dimensional relationships. That is, the surface 87 of the plug 45 and the surface 89 of the grasping portion 39 are spaced by a distance D1. Similarly, the contact portion 91 of the component 79 and the surface 93 of the member 71 are spaced by substantially the same distance D1.

When the barrel 27 and support member 71 are assembled to one another and the surfaces 89 and 93 are aligned and in abutment, the contact portion 91 bears against the surface 87 of the plug 45 and prevents plug movement (or at least prevents significant plug movement) toward the grasping portion 39. In that way, the support member 71 "backs up" or "reinforces" the plug 45 to prevent the force of the soil sample pushing against the plug 45 from rupturing the frangible section 47.

Figure 12:
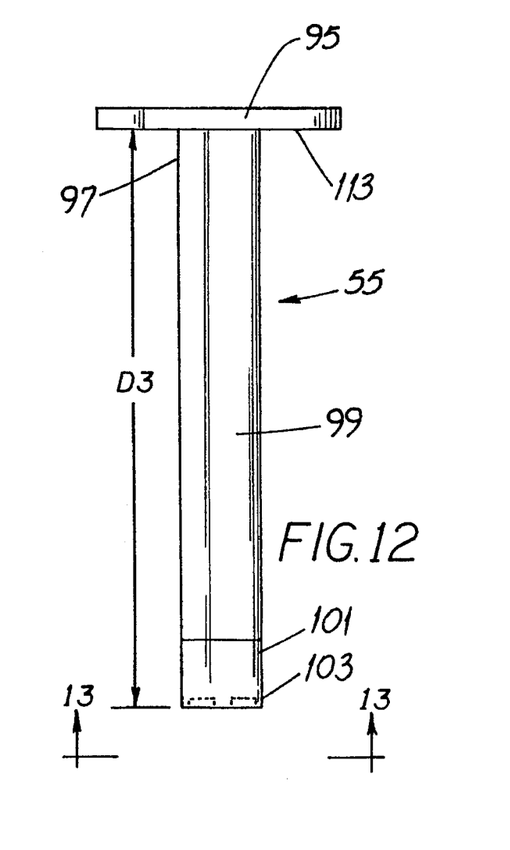
FIG. 12 is an elevation view of the expulsion device of the new tool.
Figure 13:
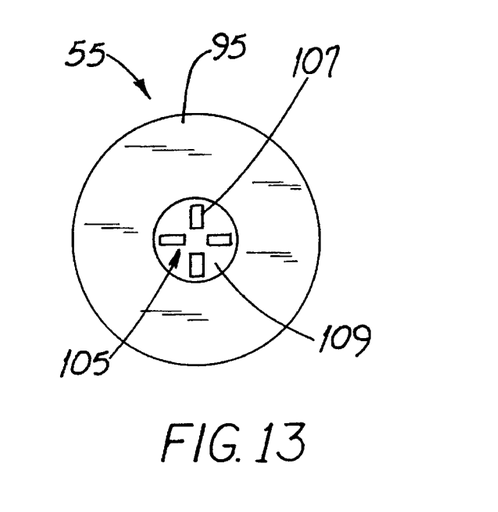
FIG. 13 is a view of the expulsion device of FIG. 12 taken generally along the viewing plane 13—13 thereof.
Figure 14:
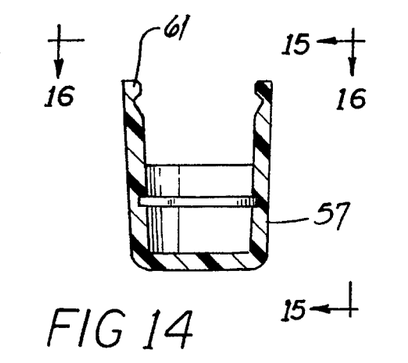
FIG. 14 is a cross-sectional elevation view of the tool cap.
Figure 15:
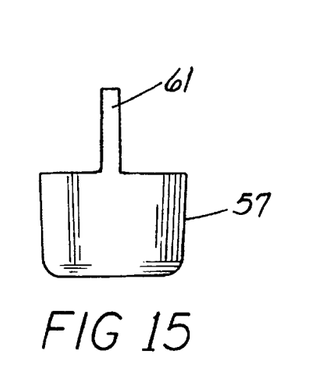
FIG. 15 is a full-representation elevation view of the cap of FIG. 14 taken generally along the viewing plane 15—15 thereof.
Figure 16:
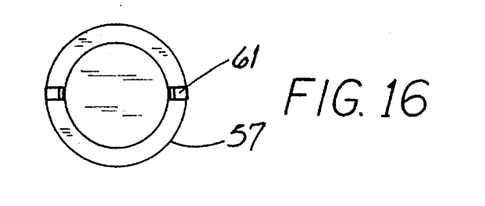
FIG. 16 is a top plan view of the cap of FIG. 14 taken generally along the viewing plane 16—16 thereof and in full representation.

Referring next to FIGS. 12 and 13, the new tool 10 also has an elongate sample expulsion device 55 for urging a soil sample out of the mouth portion 33 when such sample is being prepared for laboratory analysis or for any other reason. Such device 55 has a head 95 at its proximal end 97 and such head 95 is fixed with respect to the elongate, generally-cylindrical device body 99.

At the distal end 101 of the body 99, there is a keeper 103 which also has one or more surface deformities 105. Preferred deformities 105 include groove components 107 preferably equal in number and location to the tongue components 49a of the plug 45. Such groove components 107 (which may be said to be separated by boss-like tongue components 109) are cooperatively sized with the tongue components 49a of the plug 45 so that when the keeper 103 is urged onto the plug 45, the components 49a and 107 frictionally engage "tongue-and-groove fashion" to hold the plug 45 on the keeper 103 and prevent such plug 45 from being expelled into a vial 25 along with a soil sample 24.

And in a highly preferred embodiment, the barrel 27 and the expulsion device 55 are also cooperatively configured to have certain dimensional relationships. Specifically, the cutting edge 111 and the surface 89 of the barrel proximal end 37 are spaced at a first distance D2 from one another. The surface 113 of the device proximal end 97 and the keeper 103 of the device 55 are spaced at a second distance from one another. Such second distance D3 is greater than the first distance D2 so that the expulsion device 55 has sufficient length to urge the plug 45 (and the soil sample 24) entirely from the barrel 27 when expelling such sample 24 from the mouth portion 33.

A new method for collecting a soil sample 24 including the steps of providing a sampling tool 10 having a barrel 27, a mouth portion 33 and a plug 45 retained in the barrel 27 by a frangible section 47. The mouth portion 33 is filled with a soil sample 24 (by urging such portion into soil) and the plug 45 is urged toward the mouth portion 33, thereby breaking the frangible section 47.

In more specific aspects of the method, the filling step includes preventing the frangible section 47 from breaking and the preventing step includes contacting the plug 45 with a support member 71. The filling step is followed by the steps of fitting a cap 57 to the mouth portion 33 and engaging a cap retention arm 61 with a surface distortion 63 for holding the cap 57 on the mouth portion 33 and preventing escape of VOC vapors.

In another specific aspect of the method, the urging step includes extending the distal end 101 of the expulsion device 55 into the barrel 27, engaging the surface deformities 49, 105 with one another and expelling the soil sample 24 from the mouth portion 33. With the surface deformities 49, 105 engaged, the plug 45 is retained at the distal end 101 of the expulsion device 55 upon sample expulsion.

Figure 17:
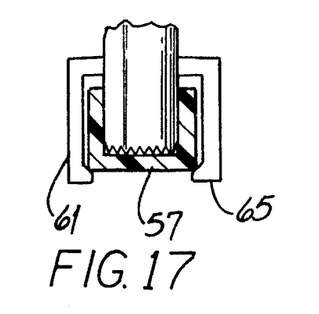
FIG. 17 is a second embodiment of a cap retention mechanism. Parts are in cross-section and other parts are broken away.
Figure 18:
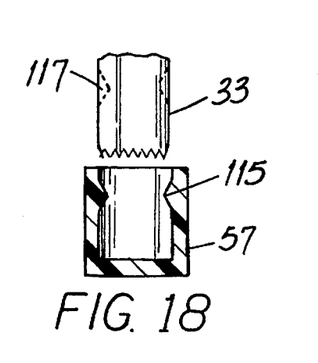
FIG. 18 is a third embodiment of a cap retention mechanism. Parts are in cross-section and other parts are broken away.

While the principles of this invention have been shown and described in connection with highly preferred embodiments, it should be understood clearly that such embodiments are by way of example and are not limiting. For example, FIG. 17 shows an arrangement in which the cap retention arms 61 are on the mouth portion 33 and the ends 65 of such arms 61 engage the bottom of the cap 57 for cap retention. FIG. 18 shows features of an alternative cap-retaining arrangement wherein radial projections 115 on the cap 57 engage depression-like notches 117 in the mouth portion 33.

Figure 19:
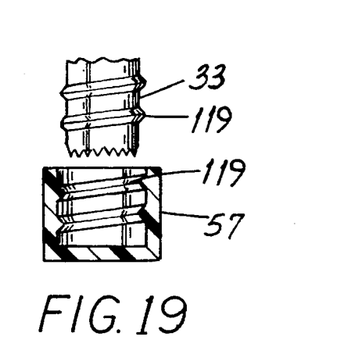
FIG. 19 is a fourth embodiment of a cap retention mechanism. Parts are in cross-section and other parts are broken away.
Figure 20:
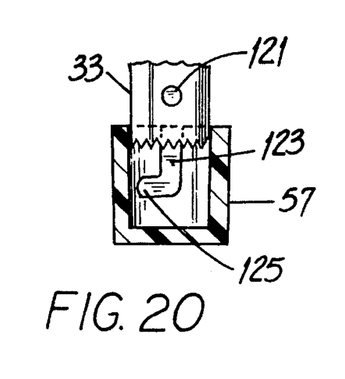
FIG. 20 is a fifth embodiment of a cap retention mechanism. Parts are in cross-section and other parts are broken away.

Or, as shown in FIG. 19, the mouth portion 33 and the cap 57 may include threads 119 for cap retention. Another approach to cap retention is shown in FIG. 20 and involves what may be referred to as a bayonet-type connection. A pin 121 protrudes from the mouth portion 33 and an L-shaped groove 123 is formed in the cap 57. After the cap 57 is inserted onto such portion 33, the cap 57 is rotated so that the pin 121 is in the portion 125 of the groove 123.

Other arrangements for holding the plug 45 to the expulsion device 55 include, as shown in FIG. 21, a plug 45 having arc-like slot members 127 and a bar piece 129 on the device 55. The bar piece 129 is rotated to engage and move into such slot members 127 as represented by the dashed outline. Or, as shown in FIG. 22, a threaded connection 131 may be used to secure the plug 45 to the device 55.

Figure 23:
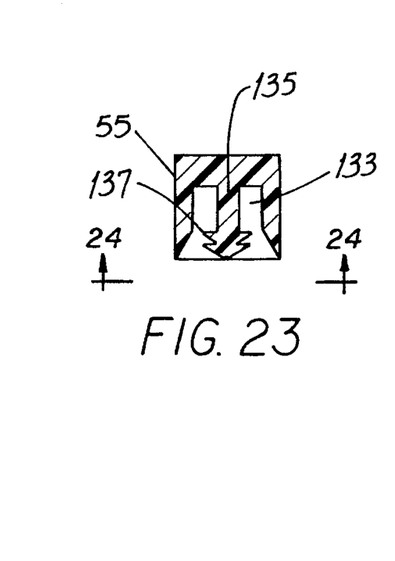
FIG. 23 is a cross-sectional elevation view of the expulsion device showing a fourth embodiment for retaining the tool plug on the expulsion device. Parts are in cross-section and broken away.
Figure 24:
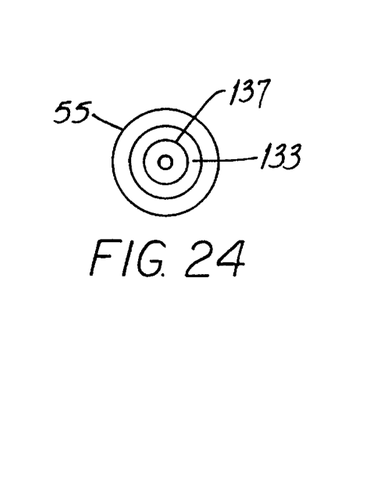
FIG. 24 is a bottom plan view of the expulsion device taken generally along the viewing plane 24—24 of FIG. 23.

FIGS. 23 and 24 show yet another arrangement for holding the plug 45 to the expulsion device 55. In this arrangement, the device 55 has an annular cavity 133 surrounding an engaging stud 135. The engaging stud 135 (which resembles an inverted pine tree in cross-section) has one or more annular teeth 137 which are flexible. When the stud 135 is urged between the tongue components 49a (or into a suitably-shaped hole or the like), such teeth 137 bear against the components 49a and prevent the plug 45 from falling into a lab vial 25.

We claim:

1. In a soil sampling tool having a barrel and a plug in the barrel for expelling a soil sample therefrom, the improvement wherein:

the barrel has a mouth portion for penetrating soil;

the plug is inside the barrel and spaced from the mouth portion;

the plug includes a frangible section integrally molded to the barrel, whereby the barrel is suitable for a single use.

2. The tool of claim 1 wherein:

the barrel includes a tubular column member;

the plug is between the mouth portion and the column member and provides an imperforate seal therebetween, whereby the plug prevents VOC vapors in the mouth portion from migrating to the column member.

3. The tool of claim 2 including a cap around the outside of the mouth portion for closing such mouth portion and wherein:

the cap is movable and removable with respect to the mouth portion;

the tool has a cap retention mechanism securing the cap with respect to the barrel.

4. The tool of claim 3 wherein:

the barrel has a longitudinal axis and an outside surface;

the cap retention mechanism includes at least one retention arm extending along the outside surface generally parallel to the axis and securing the cap with respect to the barrel.

5. The tool of claim 4 including:

a pair of retention arms attached to the cap and spaced about 180° apart;

a pair of surface distortions on the barrel for engagement by respective retention arms.

6. The tool of claim 5 wherein at least one of the surface distortions includes a tang extending from the barrel.

7. The tool of claim 6 wherein the cap has a seal engaging the mouth portion, whereby the vapors are substantially prevented from escaping from the mouth portion.

8. The tool of claim 1 including a support member contacting the plug, whereby the frangible section is prevented from breaking during collection of a soil sample.

9. The tool of claim 8 wherein:

the barrel has a grasping portion;

the support member has a holding component; and the holding component is aligned with the grasping portion during collection of a soil sample.

10. The tool of claim 9 wherein:

the grasping portion includes a lateral extension; and the holding component contacts the lateral extension during collection of a soil sample.

11. The tool of claim 1 including a sample expulsion device and wherein:

he mouth portion has a cutting edge;

the barrel has a proximal portion spaced at a first distance from the cutting edge;

the device has a distal end and a proximal portion spaced at a second distance from the distal end; and the second distance is greater than the first distance, whereby the plug may be urged from the barrel when expelling a soil sample from the mouth portion.

12. The tool of claim 11 wherein:

the plug has a surface deformity;

the distal end of the expulsion device has a surface deformity; and the surface deformities coact to retain the plug when the plug is urged from the barrel.

13. The tool of claim 12 wherein each of the surface deformities includes a tongue component and a groove component.

14. A method for collecting a soil sample including the steps of:

providing a sampling tool having a barrel, a barrel distal end, a mouth portion and a plug retained in the barrel by a frangible section;

filling the distal end with a soil sample while preventing the frangible section from breaking; and urging the plug toward the mouth portion, thereby breaking the frangible section.

15. The method of claim 14 wherein the preventing step includes contacting the plug with a support member.

16. The method of claim 14 wherein the filling step is followed by the steps of:

fitting a cap to the mouth portion; and engaging a cap retention arm with a surface distortion for holding the cap on the mouth portion.

17. The method of claim 14 wherein:

the mouth portion contains a soil sample;

the tool includes an expulsion device having a distal end and a surface deformity at the distal end;

the plug has a surface deformity;

and the urging step includes:

extending the distal end of the expulsion device into the barrel;

engaging the surface deformities with one another; and expelling the soil sample from the mouth portion, whereby the plug is retained at the proximal end of the expulsion device upon sample expulsion.

18. In a soil sampling tool having a barrel and a plug in the barrel for expelling a soil sample therefrom, the improvement wherein:

the tool includes a grasping portion;

the barrel includes a long axis and an open mouth portion;

the plug is spaced toward the grasping portion and away from the mouth portion;

the plug includes a frangible section attached to the barrel; and the tool includes a support member contacting the plug and supporting the plug along the long axis, thereby preventing the frangible section from breaking during collection of a soil sample.

19. The tool of claim 18 wherein:

the barrel includes a column member;

the plug is in the barrel between the mouth portion and the column member and provides an imperforate seal therebetween; and, the plug includes a surface deformity for engaging the support member, thereby retaining the plug on the support member while expelling a soil sample.

20. The tool of claim 19 including a cap for closing the mouth portion and wherein:

the tool has a cap retention mechanism securing the cap with respect to the barrel; and the mechanism includes a radial projection engaging a notch.

21. The tool of claim 19 wherein:

the tool has a cap retention mechanism which includes at least one retention arm extending generally parallel to the axis and securing the cap with respect to the barrel.

* * * * *